United States Patent [19]
Laure

[11] Patent Number: 4,725,280
[45] Date of Patent: Feb. 16, 1988

[54] FINGER IMPLANT

[75] Inventor: George R. Laure, Kalamazoo, Mich.

[73] Assignee: Laure Prosthetics, Inc., Portage, Mich.

[21] Appl. No.: 845,904

[22] Filed: Mar. 28, 1986

[51] Int. Cl.⁴ ............................................. A61F 2/42
[52] U.S. Cl. ..................................................... 623/21
[58] Field of Search ..................................... 623/16–23

[56] References Cited

U.S. PATENT DOCUMENTS

| | | | |
|---|---|---|---|
| 3,872,519 | 3/1975 | Giannestras et al. | 623/20 |
| 3,946,445 | 3/1976 | Bentley et al. | 623/21 |
| 4,156,296 | 5/1979 | Johnson et al. | 623/21 |
| 4,224,696 | 9/1980 | Murray et al. | 623/21 |
| 4,231,121 | 11/1980 | Lewis | 623/21 |
| 4,242,759 | 1/1981 | White | 623/21 |
| 4,353,136 | 10/1982 | Polyzoides et al. | 623/21 |
| 4,375,703 | 3/1983 | Evans et al. | 623/21 |
| 4,385,404 | 5/1983 | Sully et al. | 623/21 |
| 4,470,158 | 9/1984 | Pappas et al. | 623/21 |
| 4,568,348 | 2/1986 | Johnson et al. | 623/20 |

FOREIGN PATENT DOCUMENTS

| | | | |
|---|---|---|---|
| 3312556 | 10/1983 | Fed. Rep. of Germany | 623/20 |
| 2302717 | 11/1976 | France | 623/20 |

Primary Examiner—Richard J. Apley
Assistant Examiner—David J. Isabella
Attorney, Agent, or Firm—Flynn, Thiel, Boutell & Tanis

[57] ABSTRACT

A prosthetic joint for replacing a finger joint, including a shell-like member which is secured to the distal end of one phalanx, this shell-like joint having a vertical cross section which resembles a semicylindrical shell. The shell preferably has parallel legs extending rearwardly from the edges of the semicylindrical portion, with the lowermost leg having a greater rearward extension. The shell has a transverse cross section which results in two convex bearing surfaces symmetrically positioned relative to the central vertical plane of the shell. These convex bearing surfaces define a groove therebetween at the central vertical plane. The other joint member includes a tack portion which extends into the other phalanx, which tack portion has an enlarged head provided with a concave bearing surface for engagement with the exterior bearing surface on the shell. The concave bearing surface is provided by a pair of sidewardly positioned bearing parts which are symmetrical about an intermediate ridge which extends along the central vertical plane of the head. The bearing parts of the head have a surface configuration compatible with the bearing surfaces of the shell.

5 Claims, 7 Drawing Figures

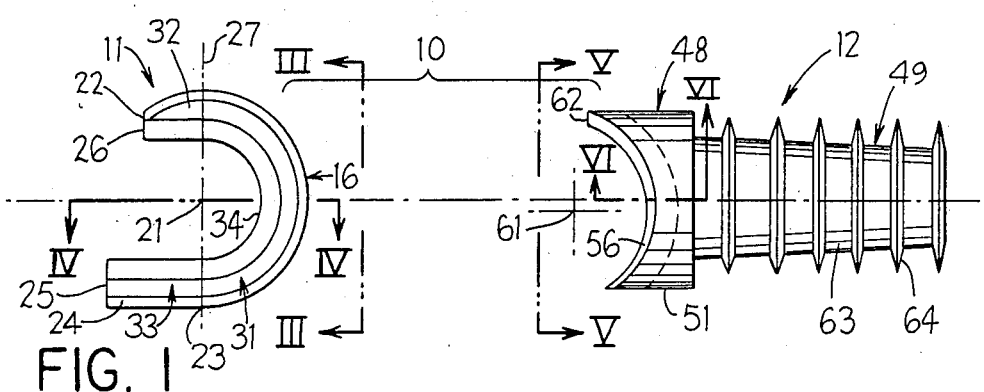
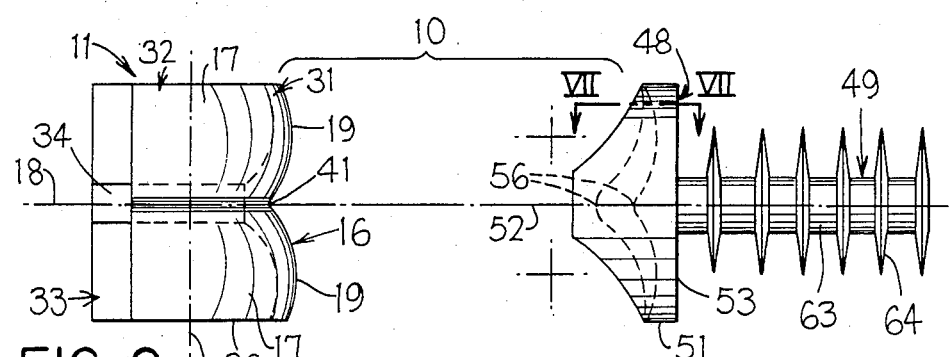
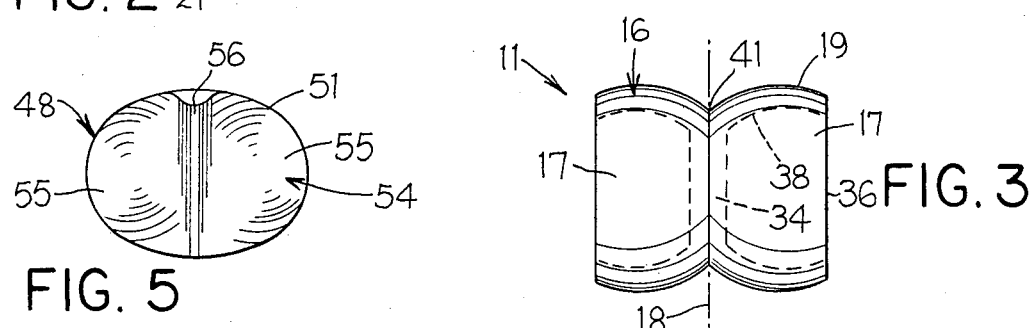
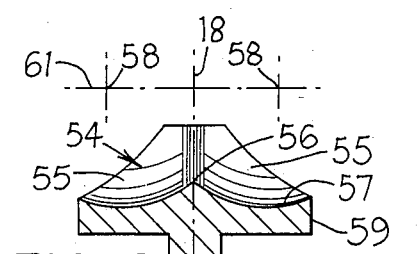
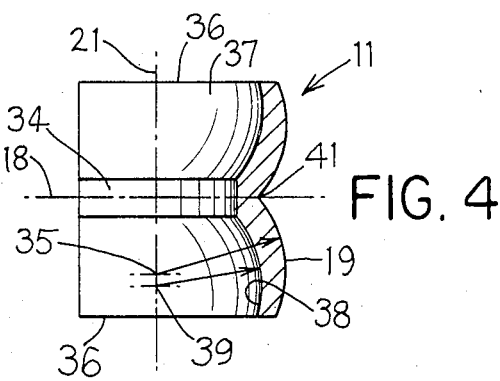
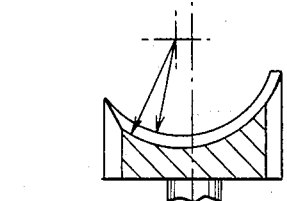

FINGER IMPLANT

FIELD OF THE INVENTION

This invention relates to a prosthetic joint adapted to replace a human joint and, more specifically, to an improved prosthetic joint adapted to replace either the proximal or distal phalangeal joint of the finger.

BACKGROUND OF THE INVENTION

Numerous prosthetic joints have been developed for replacing finger joints, although most such joints have involved the replacement of the joint where the finger joins the hand, namely the joint between the proximal phalanx and the metatarsal. These latter joints typically involve some type of captivated ball-and-socket arrangement for permitting a substantial range of pivoting movement in a vertical plane, while sometimes also permitting a limited sideward displacement in an attempt to provide for motion which more closely correlates with the natural joint. Joints of this latter type, however, are normally not suitable for replacing the proximal or distal phalangeal joints of the finger inasmuch as these latter replacement joints typically possess a structure which is undesirably large and complex for replacing the phalangeal joints, and in addition these latter joints do not require and in fact do not desire any capability of providing a sideward or lateral pivoting.

Examples of finger joints which are designed specifically for replacing the human joint located between the metatarsal and the proximal phalanx are disclosed by U.S. Pat. Nos. 3,946,445, 4,242,759 and 4,231,121, although the joint of this latter patent is also disclosed as being suitable for use as a PIP (phalangeal-interphalangeal) or DIP (distal-interphalangeal) joint.

Accordingly, the present invention relates to an improved joint which is designed specifically for use in replacing the human joint located between the proximal and intermediate phalanx (a PIP joint), or between the intermediate and distal phalanx (a DIP joint). The improved prosthetic joint of this invention is particularly of a small and compact structure to permit its surgical implantation so as to replace the natural joint, with the joint being implantable in such a manner as to facilitate its attachment to the phalanx while at the same time providing a vertical range of pivoting movement which closely approximates the natural joint movement while restricting undesired sideward movement.

In the improved implant joint of this invention, the joint is defined by two one-piece implant members, one comprising essentially a cap member having a configuration which roughly resembles a semicylindrical shell-like element which has a substantially planar rearward extension associated with the lower edge thereof, whereby the member can be attached to the distal end of the respective phalanx and oriented so that the outer substantially semicylindrical surface of the member is generated about a substantially horizontal axis. The outer surface of the member has a substantially centrally located groove extending therearound for accommodating a rib on the other implant member to prevent relative sideward pivoting between the joint members. The other joint member includes an enlarged head secured to one end of a tack which has deformable flanges so that the tack can be inserted into and lockingly secured to the proximal end of the adjacent phalanx. The enlarged cap on this other implant member has a pair of sidewardly spaced part-spherical surfaces which are mirror images of one another and are effectively separated by an intermediate ridge, which ridge projects into the groove on the first member. The bearing surfaces on the first member have a configuration which, in transverse cross section, corresponds to the bearing surfaces on the second member so as to permit free and smooth slidable support and contact between the first and second members, with the slidable contact restricting relative movement between the members to pivoting movement substantially within a vertical plane.

Other objects and purposes of the improved joint according to the present invention will be apparent to persons familiar with joints of this general type upon reading the following specification and inspecting the accompanying drawings.

BRIEF DESCRIPTION OF THE DRAWINGS

FIG. 1 is a side view showing the two components of the joint according to the present invention in a separated condition for purposes of illustration.

FIG. 2 is a top view of the joint shown in FIG. 1.

FIGS. 3, 4, 5 and 6 are views taken substantially along lines III—III, IV—IV, V—V and VI—VI, respectively, in FIG. 1.

FIG. 7 is a sectional view as taken substantially along line VII—VII in FIG. 2.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to the geometric center of the joint and designated parts thereof. Said terminology will include the words specifically mentioned, derivatives thereof, and words of similar import.

DETAILED DESCRIPTION

Referring to the drawings, and specifically FIGS. 1 and 2, there is illustrated an implantable finger joint 10 according to the present invention, which joint is designed specifically for use as a PIP or DIP joint. This joint is created by two members, namely a first one-piece implant member 11 and a second one-piece implant member 12. The first member 11 can be constructed either of a plastic material such as a high molecular weight polyethylene or of an F-75 approved metal such as a high chrome molybdenum alloy. The second implant member 12, due to its preferred construction, is of a plastics material, preferably an ultra-high molecular weight polyethylene.

The first member 11 is intended to be implanted onto the distal end of the respective phalanx and is constructed so as to resemble a hollow shell of substantially semicylindrical configuration when viewed in vertical cross section as illustrated in FIG. 1. When viewed in horizontal cross section, however, as appearing in FIG. 4, the first implant member or shell 11 has a cross section which resembles a shallow or flattened V. When viewed in this latter cross section, the member or shell 11 defines thereon a smooth outer bearing surface 16 of a convex configuration, this bearing surface 16 being divided into two identical parts 17 which are mirror images of one another and located directly opposite and projecting outwardly from opposite sides of the central vertical plane 18. Each of these surfaces 17 is generated by means of an arcuate line 19 which projects sidewardly away from the plane 18, with these lines 19 being rotated about the horizontal axis 21 so as to generate the symmetrical surfaces 17. The lines 19 are generated or rotated about the axis 21 through an angle which extends from the uppermost free edge or extremity 22 clockwise in FIG. 1 to a tangency point 23, which angle exceeds 180°, and preferably is in the range of about 225°, with the point of tangency 23 being located substantially within the vertical plane 27 containing the axis of rotation 21. From the tangency point 23, however, the lines 19 are then moved rearwardly (leftwardly in FIG. 1) along a straight path through a distance so as to generate extended lower bearing surfaces 24 which are tangentially joined to and constitute extensions of the bearing surfaces 17. These latter surfaces 24 extend rearwardly through a distance so as to terminate in a free end surface 25, the latter being spaced rearwardly beyond the end surface 26 associated with the upper free end of the shell.

The first member or shell 11, as described above, has a substantially U-shaped configuration with the base or bight 31 of the U extending through 180° as defined rightwardly of the vertical plane 27 which contains the rotational axis 21, with this bight portion 31 having a rearwardly projecting upper leg portion 32 and a rearwardly projecting lower leg portion 33, the latter projecting through a greater extent than the upper leg portion 32. The outer bearing surface 16 on the upper leg portion 32 is generated about the central axis 21 as described above, but the inner surface of this upper leg portion is straight and extends outwardly in generally parallel relationship to the inner surface of the lower leg portion 33. Due to the configuration of the bearing surface 16, and the fact that the wall of the shell is of substantially uniform thickness, this results in the inner surface of the shell defining an inwardly projecting rib 34 which is positioned centrally of the shell substantially along the central plane 18, with this rib extending throughout substantially the full length of the inner surface of the shell. This rib functions as a locking member for permitting the shell to be lockingly secured onto the distal end of the respective phalanx. Further, due to the rearward extension created by the lower leg portion 33, this enables the shell to project rearwardly along a greater extent of the lower surface of the distal end of the respective phalanx, and hence provide greater strength and rigidity for the joint, particularly since the dominant pivoting movement of the joint is a downward pivoting of the member 12 about the member 11.

The lines 19 used to generate the surfaces 17 are themselves generated about equal radii generated about different center points. For example, as appearing in FIG. 4, each line 19 is generated about a center point 35 which is located on the center axis 21 but is displaced sidewardly from the central plane 18. More specifically, the center point 35 for each respective line 19 is displaced from the plane 18 by a distance which is slightly past the midway point between the plane 18 and the respective outer edge surface 36.

The shell has an inner surface 37 which is formed similar to the outer surface 17 in that it is generated by means of an arcuate line 38, this latter line being generated by means of a radius swung about a center point 39 which is positioned close to but spaced outwardly from the center point 35. The center point 39 is located on the center line 21, and the surface 37 is generated by rotating line 38 about the centerline 21.

The manner in which the mirror image surfaces 17 are formed results in the bearing surface 16 having a groove 41 defined at the intersection of the surfaces 17, this groove hence being substantially V-shaped in cross section and extending throughout the outer surface of the shell substantially along the central plane 18 thereof. The lines 38 defining the inner surface 37 are generated about the center axis 21 solely through an angle of 180°, as bounded by the vertical plane 27, whereupon the lines 38 as they project rearwardly (leftwardly) of this plane 27 are then moved along a straight path so that the inner surfaces of the leg portions 32 and 33 are straight and parallel to one another.

Considering now the second member 12, which member will hereinafter be referred to as the tack member, it is formed by two basic parts which are integrally joined together, namely an enlarged head part 48 and an outwardly projecting tack part 49.

Considering first the head part 48, it has an outer annular peripheral surface 51 which is of an elongated elliptical configuration. This elliptical configuration 51 is horizontally or sidewardly elongated, that is, the major axis of the ellipse extends perpendicular to the central vertical plane 18, with the shorter or minor axis of the ellipse being disposed substantially within the central vertical plane 18. The centerline or axis 52 of the ellipse is disposed within the plane 18 and, when extended, intersects the horizontal centerline or axis 21. The head part 48 defines a substantially planar rear surface 53 on the end thereof remote from the shell 11, which surface 53 extends substantially perpendicular to the centerline 52.

The face end of the head part 48, namely that end which is directly opposed to the shell 11, has a smooth part-spherical concave bearing surface 54 thereon adapted for slidable support and engagement with the bearing surface 16 of the shell 11. The bearing surface 54, like that of the bearing surface 16, is divided into two parts 55 which are disposed side-by-side and are mirror images of one another. These bearing surface parts 55, due to the manner in which they are generated as explained below, result in the defining of a rib or ridge 56 therebetween, this ridge 56 being disposed substantially within the central vertical plane 18 and hence being positioned so as to be accommodated within the groove 41 of the shell 11.

Each of the surfaces 55 is initially defined by an arcuate line 57 which extends sidewardly away from the central plane 18. This line 57 is generated on a uniform radius about a center point 58, which center point is sidewardly displaced from the central plane 18 so as to be disposed between the plane 18 and a further parallel plane defined by the outermost edge 59 of the head part. In fact, the location of the center point 59 and the radius from this center point to the line 57 is identical to the relationship which exists between the center point 35 and the line 19, whereby the line 57 has an identical curvature to that of the line 19. These center points 58 are hence located on an axis of revolution 61 which, when the parts 11 and 12 are fitted together, results in the axis 61 being disposed within the vertical plane 27 but spaced downwardly in parallel relationship from the axis 21. The axis 61 is spaced downwardly below the centerline 52, as illustrated in FIG. 1, so that the surfaces 55 as generated about the axis 61 will not be symmetrical above and below the central horizontal plane defined by the axis 52, but rather will be nonsymmetrical relative to the horizontal plane containing the axis 52 so that the upper end 62 of the rib 56 hence projects rearwardly through a greater extent than the lower end thereof. This upper end 62 is provided with an appropriate rounded curvature for merger with the exterior peripheral surface 51.

The nonsymmetrical curvature created by the upper and lower portions of the bearing surfaces 55 is significant with respect to proper slidable engagement and support of the bearing surfaces 55 on the bearing surfaces 17 and, more significantly, facilitates the downward pivoting of the tack member 12 relative to the shell 11 from the aligned position of FIG. 1 through an angle of approximately 90° so as to facilitate the desired natural pivoting movement of the PIP or DIP joint.

Considering now the tack part 49, it includes a projecting stem 63 which projects outwardly from the rear surface 53 through a distance which exceeds the axial thickness of the head part 48. This stem 63 has the centerline thereof aligned with the longitudinal centerline 52, and the stem 63 is of substantially elliptical cross section in that it is of substantial vertical extent as illustrated in FIG. 1, but is relatively narrow when considered in horizontal cross section as appearing in FIG. 2. The stem has a plurality of circular annular flexible flanges 64 integrally formed thereon and projecting radially therefrom in axially spaced relationship. These flanges 64 are preferably of a thinning or tapered cross section as they project outwardly so as to be resiliently flexible, whereupon insertion of the stem into the proximal end of the respective phalanx will result in these flanges 64 suitably deforming so as to automatically lock the joint member 12 to the respective phalanx.

OPERATION

While the operation of the joint 10 is believed apparent from the description set forth above, nevertheless same will be briefly described to ensure a complete understanding thereof.

To surgically implant the joint 10, the opposed ends of the respective phalanx will be surgically removed so as to provide the additional space required by the joint 10. The shell 11 will be inserted over the distal end of the innermost phalanx so that the shell is disposed with the axis 21 oriented substantially horizontally relative to the finger when the finger is oriented horizontally. The shell 11 is positioned so that the lower rearwardly extending leg 33 extends along the lower part of the phalanx, and the rib 34 is effective to permit the shell to be securely and stationarily locked to the phalanx so as to prevent any relative movement therebetween.

The tack member 12 is also fixedly secured to the proximal end of the adjacent phalanx, with the stem 63 being inserted into the phalanx and locked in position by means of the deformable flanges 64. Bone seed may also be used to facilitate long-term securement.

After the members 11 and 12 have been appropriately secured to the respective phalanx, the opposed bearing surfaces 16 and 54 are positioned in direct supportive and slidable engagement with one another, whereupon the rib 56 projects into the groove 41, and this rib-groove cooperation in conjunction with the curvature of the opposed bearing surfaces effectively prevents any relative sideward pivoting between the joined members. At the same time, however, the slidable engagement of the smooth part-spherical bearing surfaces 55 with the respective bearing surfaces 17, which surfaces 17 and 55 have identical contours, permits the tack member 11 to freely vertically slidably move on the bearing surface 16, which movement in effect occurs about the axis 21 and hence functions as a vertical pivoting movement about this latter axis. Since each bearing surface 16 and 54 is defined by two sidewardly related surface parts which are mirror images of one another, with each of these surface parts 17 and 55 itself being a part-spherical surface which is a mirror image of its companion part, this hence provides a significantly large bearing surface which not only greatly controls and provides for desired pivoting joint movement solely within a substantially vertical or single plane, but this relationship also provides significant slidable contact area within an extremely small joint structure. The configuration of the exterior bearing surfaces on the shell 11, and the cooperating configuration of the bearing surfaces on the tack member 12, also permit relative pivoting in the vertical plane through an angle which closely approximates 90°, and in particular permits the tack member 12 to be vertically swung downwardly into a position wherein it projects substantially downwardly from the shell 11, this being permissible by the contour of the bearing surfaces and at the same time still results in a strong and durable joint in view of the manner in which the shell is provided with the rearward extension associated with the lower leg portion 33 thereof.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a prosthetic finger joint for replacing a human finger joint between the intermediate phalanx and the distal or proximal phalanx, said prosthetic finger joint consisting solely of two one-piece members which cooperatively and pivotally engage one another to permit relative pivoting therebetween substantially solely within a single plane, a first said one-piece member being fixedly attached to one end of a first said phalanx and a second said one-piece member being fixedly attached to an opposed end of a second said phalanx, the improvement comprising:

said first one-piece member comprising a shell having a substantially U-shaped vertical cross section, said shell having a bight portion which resembles a semi-cylindrical element and defines thereon a convex exterior bearing surface which is of substantial horizontal extend and which is generated on a first radius about a substantially horizontal extending center axis so as to define said convex bearing surface, said convex bearing surface being defined by two bearing surface parts which are disposed side-by-side and are located on opposite sides of a central vertical plane which divides said shell into identical halves, said bearing surface parts being mirror images of one another on opposite sides of said central vertical plane, each of said bearing surface parts also having a curved convex configuration in a transvere plane which is perpendicular to said central vertical plane, and said bearing surface parts meeting substantially at said central vertical plane and defining a shallow groove which extends around the exterior convex bearing surface substantially within said central vertical plane;

said shell defining said first one-piece member also including upper and lower leg portions which project outwardly from the respective upper and lower extremities of the bight portion, said upper and lower leg portions extending generally parallel with one another, said lower leg portion extending outwardly through a greater extend than said upper leg portion, said upper and lower leg portions defining thereon external bearing surfaces which constitute an extension of the exterior bearing surface of said bight portion and which have trnasverse configurations which correspond to the transverse configuration of said convex bearing surface, the external bearing surface associated with said upper leg portion constituting a continous extension of the convex bearing surface defined on said bight portion and being generated substantially about said center axis, and the external bearing surface associated with said lower leg constituting a continuous extension of the convex bearing surface defined on said bight portion and extending along a straight line path which is substantially tangential to the bearing surface of the bight portion;

said second one-piece member being of a high-density plastic material and comprising an enlarged head part having a stem projecting outwardly therefrom for securement within said second phalanx;

said head part defining on the exposed end thereof a smoothly curved concave bearing surface having a configuration compatible with that of the convex bearing surface on said first member, said concave bearing surface in vertical cross section being generated about a second radius equal to said first radius, said concave bearing surface including two identical bearing surface parts which are disposed on opposite sides of said central vertical plane and are mirror images of one another relative to said central vertical plane, each of said bearing surface parts having a smoothly curved transverse concave configuation with said bearing surface parts being joined together substantially at said central vertical plane and defining thereat an outwardly projecting ridge which extends vertically across said head part;

said head part having a transvere cross section which is generally eliptical;

said stem having a transverse cross section which is also generally eliptical, the transverse cross section of said stem being substantially smaller than the transverse cross section of said head part;

said stem having a plurality of encircling flanges provided thereon and projecting outwardly therefrom in substantially uniformly axially spaced relationship therealong, said flanges being resiliently deformable for lockingly securing said stem to the respective phalanx;

said first and second one-piece members being pivotally slidably and supportingly engaged due to the concave bearing surface parts being directly slidably and supportably engaged with the respective convex bearing surface parts and with said ridge being slidably seated within said shallow groove.

2. A joint according to claim 1, wherein said shell is of substantially uniform wall thickness and defines thereon a ridge which extends along the central vertical plane and projects outwardly from the inner surface of the shell due to formation of the shallow groove in the exterior surface of the shell.

3. A joint according to claim 1, wherein the concave bearing surface on said second member is generated about a transverse axis which is spaced downwardly from a central axis which extends longitudinally through the second member.

4. A joint according to claim 1, wherein the transverse convex configurations on the convex bearing surface parts are respectively generated about center points which are disposed on said center axis but disposed equally spaced on opposite sides of said central vertical plane.

5. A joint according to claim 1, wherein said encircling flanges associated with the stem are of a substantially circular configuration in relationship to the eliptical cross section of the stem.

* * * * *

UNITED STATES PATENT AND TRADEMARK OFFICE
CERTIFICATE OF CORRECTION

PATENT NO. : 4 725 280
DATED : February 16, 1988
INVENTOR(S) : George R. Laure

It is certified that error appears in the above-identified patent and that said Letters Patent is hereby corrected as shown below:

Column 6, line 62; change "transvere" to ---transverse---.

Column 7, line 12; change "trnasverse" to ---transverse---.

Column 8, line 3; change "transvere" to ---transverse---.

Signed and Sealed this

Nineteenth Day of July, 1988

Attest:

DONALD J. QUIGG

Attesting Officer      Commissioner of Patents and Trademarks